United States Patent
Trescony et al.

(10) Patent No.: US 9,861,799 B2
(45) Date of Patent: Jan. 9, 2018

(54) CEREBROSPINAL FLUID SHUNT HAVING LONG TERM ANTI-OCCLUSION AGENT DELIVERY

(75) Inventors: Paul V. Trescony, Champlin, MN (US); Edouard Koullick, Golden Valley, MN (US)

(73) Assignee: MEDTRONIC PS MEDICAL, INC., Goleta, CA (US)

( * ) Notice: Subject to any disclaimer, the term of this patent is extended or adjusted under 35 U.S.C. 154(b) by 888 days.

(21) Appl. No.: 12/607,419

(22) Filed: Oct. 28, 2009

(65) Prior Publication Data

US 2010/0042039 A1  Feb. 18, 2010

Related U.S. Application Data (62) Division of application No. 11/380,157, filed on Apr. 25, 2006, now abandoned.

(51) Int. Cl.
*A61M 5/00* (2006.01)
*A61M 25/14* (2006.01)
(Continued)

(52) U.S. Cl.
CPC ........... *A61M 27/006* (2013.01); *A61L 31/16* (2013.01); *A61M 25/007* (2013.01);
(Continued)

(58) Field of Classification Search
CPC ........ A61M 27/006; A61M 2025/0056; A61M 2025/0057; A61M 2210/0693;
(Continued)

(56) References Cited

U.S. PATENT DOCUMENTS 3,598,127 A * 8/1971 Wepsic .................. 604/265
3,683,929 A   8/1972 Holter
(Continued)

FOREIGN PATENT DOCUMENTS

| EP | 1 649 880 A | 4/2006 |
|---|---|---|
| WO | WO 2004/073768 A | 9/2004 |
| WO | WO 2006/015091 A | 2/2006 |

OTHER PUBLICATIONS

Eric W.P. Damen, et al. "Paclitaxel esters of malic acid as prodrugs with improved water solubility." Bioorganic & Medicinal Chemistry, vol. 8, Issue 2, Feb. 2000, pp. 427-432, ISSN 0968-0896, 10.1016/S0968-0896(99)00301-6. (http://www.sciencedirect.com/science/article/pii/S0968089699003016) accessed Sep. 11, 2012.*
(Continued)

*Primary Examiner* — Adam Marcetich
(74) *Attorney, Agent, or Firm* — Patterson Thuente Pedersen, P.A.

(57) ABSTRACT

A shunt for at least partial implantation into a patient that includes an elongated conduit having at least one lumen therethrough and a second lumen concentric about the first lumen along at least part of the first lumen, that includes a proximal end for receipt of bodily fluids for flow through the shunt and a distal end for discharge of the bodily fluids from the shunt, and a long term source of at least one occlusion resistant agent, wherein said at least a portion of the at least one occlusion resistant agent can permeate through at least a portion of the elongated conduit. The invention also includes kits and systems.

12 Claims, 3 Drawing Sheets

(51) Int. Cl.
  *A61M 27/00* (2006.01)
  *A61L 31/16* (2006.01)
  *A61M 25/00* (2006.01)

(52) U.S. Cl.
  CPC ..... *A61L 2300/41* (2013.01); *A61L 2300/416* (2013.01); *A61L 2300/42* (2013.01); *A61M 2025/0019* (2013.01)

(58) Field of Classification Search
  CPC ........ A61M 25/0045; A61F 2250/0067; A61F 2250/0068; A61F 2/07
  USPC ..... 604/8, 9, 10, 93.01, 99.02, 99.03, 99.04, 604/103.01, 140, 141, 142, 191, 244, 25, 604/7, 264, 265, 266, 269; 623/1.39, 1.4, 623/1.42, 1.43, 1.44, 1.45
  See application file for complete search history.

(56) References Cited

U.S. PATENT DOCUMENTS

| | | |
|---|---|---|
| 3,889,687 A | 6/1975 | Harris et al. |
| 4,186,745 A * | 2/1980 | Lewis ............... A61L 29/041 604/265 |
| 4,364,395 A | 12/1982 | Redmond et al. |
| 4,578,057 A | 3/1986 | Sussman |
| 4,605,395 A | 8/1986 | Rose et al. |
| 4,610,658 A | 9/1986 | Buchwald et al. |
| 4,623,329 A * | 11/1986 | Drobish et al. ............. 604/29 |
| 4,698,058 A | 10/1987 | Greenfield et al. |
| 4,722,906 A | 2/1988 | Guire |
| 4,741,730 A | 5/1988 | Dormandy et al. |
| 4,755,171 A * | 7/1988 | Tennant ............... A61F 2/04 604/265 |
| 4,787,886 A | 11/1988 | Cosman |
| 4,816,016 A | 3/1989 | Schulte et al. |
| 4,861,331 A | 8/1989 | East et al. |
| 4,867,740 A | 9/1989 | East |
| 4,883,456 A | 11/1989 | Holter |
| 4,916,193 A | 4/1990 | Tang et al. |
| 4,973,493 A | 11/1990 | Guire |
| 4,979,959 A | 12/1990 | Guire |
| 4,994,071 A | 2/1991 | MacGregor |
| 5,000,731 A | 3/1991 | Wong et al. |
| 5,002,582 A | 3/1991 | Guire et al. |
| 5,112,303 A | 5/1992 | Pudenz et al. |
| 5,217,492 A | 6/1993 | Guire et al. |
| 5,221,698 A | 6/1993 | Amidon et al. |
| 5,258,041 A | 11/1993 | Guire et al. |
| 5,263,992 A | 11/1993 | Guire |
| 5,300,059 A * | 4/1994 | Rubinstein et al. .......... 604/408 |
| 5,304,121 A | 4/1994 | Sahatjian |
| 5,336,166 A | 8/1994 | Sierra |
| 5,464,650 A | 11/1995 | Berg et al. |
| 5,512,329 A | 4/1996 | Guire et al. |
| 5,697,951 A | 12/1997 | Harpstead et al. |
| 5,741,551 A | 4/1998 | Guire et al. |
| 5,858,653 A | 1/1999 | Duran et al. |
| 5,873,865 A | 2/1999 | Horzewski et al. |
| 5,925,054 A | 7/1999 | Taylor et al. |
| 5,942,555 A | 8/1999 | Swanson et al. |
| 6,030,358 A | 2/2000 | Odland |
| 6,077,698 A | 6/2000 | Swan et al. |
| 6,096,019 A * | 8/2000 | Andrews ................. 604/500 |
| 6,110,155 A | 8/2000 | Baudino |
| 6,121,027 A | 9/2000 | Clapper et al. |
| 6,214,022 B1 | 4/2001 | Taylor et al. |
| 6,214,901 B1 | 4/2001 | Chudzik et al. |
| 6,278,018 B1 | 8/2001 | Swan |
| 6,344,035 B1 | 2/2002 | Chudzik et al. |
| 6,348,042 B1 | 2/2002 | Warren, Jr. |
| 6,603,040 B1 | 8/2003 | Swan |
| 6,626,902 B1 | 9/2003 | Kucharczyk et al. |
| 6,706,408 B2 | 3/2004 | Jelle |
| 6,926,735 B2 * | 8/2005 | Henderson ............... 623/1.42 |
| 7,322,954 B2 | 1/2008 | Putz |
| 2002/0026138 A1 | 2/2002 | Cowan et al. |
| 2002/0123713 A1 * | 9/2002 | Watson ..................... 604/8 |
| 2003/0130206 A1 * | 7/2003 | Koziak et al. ............ 514/23 |
| 2003/0167031 A1 * | 9/2003 | Odland ..................... 604/8 |
| 2003/0171738 A1 | 9/2003 | Konieczynski et al. |
| 2003/0187367 A1 | 10/2003 | Odland |
| 2004/0030218 A1 * | 2/2004 | Kocur et al. .............. 600/36 |
| 2004/0068241 A1 * | 4/2004 | Fischer, Jr. ............ A61F 2/82 604/265 |
| 2004/0073157 A1 * | 4/2004 | Knudson et al. ............. 604/8 |
| 2004/0210208 A1 * | 10/2004 | Paul ................... A61M 25/00 604/500 |
| 2004/0220510 A1 | 11/2004 | Koullick et al. |
| 2005/0079199 A1 * | 4/2005 | Heruth et al. ............ 424/423 |
| 2005/0085777 A1 * | 4/2005 | Tan .................... A61L 29/16 604/265 |
| 2005/0100580 A1 * | 5/2005 | Osborne ............... A61L 29/085 424/424 |
| 2005/0208092 A1 | 9/2005 | Falotica et al. |
| 2006/0004317 A1 | 1/2006 | Mauge et al. |
| 2006/0025752 A1 * | 2/2006 | Broaddus et al. .......... 604/537 |
| 2006/0247569 A1 | 11/2006 | Bertrand et al. |
| 2006/0251710 A1 * | 11/2006 | Kwon et al. ............. 424/450 |
| 2006/0258970 A1 | 11/2006 | Moskowitz et al. |
| 2007/0038292 A1 * | 2/2007 | Danielpour ............. A61F 2/82 623/1.42 |
| 2007/0129394 A1 * | 6/2007 | Sharma et al. ............ 514/291 |

OTHER PUBLICATIONS

Drug Digest, Drugs & Vitamins, Drug Library, *Urokinase*, 3 pgs., product description.
ICU AU Procedural Manual, *Steptokinase*, 4 pgs.
Medtronic, Inc., *Cranial Repair*, product description, 4 pgs.
Streptase Pharmacology, Pharmacokinetics, Studies, Metabolism, *Clinical Pharmacology*, 3 pgs., product description.
Webpage www.netdoctor.co.uk/medicines, *Streptokinase*, 2 pgs.

* cited by examiner

CEREBROSPINAL FLUID SHUNT HAVING LONG TERM ANTI-OCCLUSION AGENT DELIVERY

RELATED APPLICATION

This application is a divisional of and claims priority to U.S. patent application Ser. No. 11/380,157, Trescony et al, Cerebrospinal Fluid Shunt Having Long Term Anti-Occlusion Agent Delivery, filed Apr. 25, 2006.

FIELD

This invention relates to shunts and techniques to prevent blockage or occlusion of such a shunt. One embodiment of the invention relates to a cerebrospinal fluid shunt.

BACKGROUND

Hydrocephalic shunts are designed to remove excess fluid from the ventricular region of the brain to a different internal location, such as the peritoneal cavity. Alternatively, cerebral spinal fluid (CSF) shunts may have a proximal end placed into the patient's ventricular region and a distal end being connected external of the patient. In either configuration, a common problem involves the immune response and/or an inflammatory response of the patient or inflammatory response to the insertion of the foreign body, i.e., the catheter, therein. Additionally, occlusion of the catheter lumens often occur and preclude effective drainage of the CSF fluid. It is estimated that 40% of implanted hydrocephalic shunts fail within 5 years due to tissue proliferation into the shunt lumen.

U.S. Pat. No. 6,110,155, issued to Baudino, and commonly owned by Applicant of the present application, shows an anti-inflammatory agent loaded catheter distal tip and method for preventing tissue fibrosis. The device and method utilizes, in one embodiment, dexamethasone sodium phosphate agent on a ventricular catheter tip to prevent encapsulation of the catheter. U.S. Pat. No. 6,348,042 B1, issued to Warren, Jr., discloses a bio-active shunt device and method by which the interior lumen surface of a shunt is coated with a matrix forming system having at least one enzyme configured for inciting activity to preclude the growth of obstructing cellular material. In one embodiment, the interior surface of the catheter lumen is impregnated with proteases or a matrix containing proteases that is impregnated onto the wall of the lumen to degrade cellular material including cells of the choroid plexus and peritoneum.

U.S. Pat. Pub. No. US 2004/0220510, commonly assigned, discloses an occlusion resistant shunt for implantation into a patient to treat hydrocephalus. The shunts are constructed to include one or more occlusion resistant materials. Shunts for the treatment of hydrocephalus may remain implanted for the lifetime of a patient, therefore there remains a need for an extended duration of local delivery of agents to limit or prevent occlusion.

SUMMARY

An occlusion resistant medical shunt, particularly a hydrocephalic shunt, is provided for implantation into a mammal. The shunt has an elongate wall structure configured as a tube having a lumen therethrough and a proximal end for receipt of bodily fluids. The bodily fluids, such as cerebrospinal fluid, flows through the shunt to a distal end for discharge of the bodily fluids. The wall structure of the shunt generally includes a biocompatible medical device material. The shunts of the present invention allow for long term delivery of one or more occlusion resistant materials to resist occlusion of the lumenal passage of the shunt.

A fully implanted medical shunt of the invention for use as a hydrocephalus shunting device has a construction which controls the immunologic response that the recipient may experience after receipt of the shunt within the recipient's body, and through the lifetime of the implantation, which is often the lifetime of the patient. In various embodiments of the present invention, the shunt comprises an elongate wall structure configured as a tube having a lumen therethrough and a proximal end for receipt of bodily fluids and a distal end for discharge of said bodily fluids into another portion of the recipient's body. In one embodiment, the proximal end is located in the ventricular region of the brain and the distal end is located in the peritoneal structure at the abdomen. In another embodiment, the proximal end is located in the ventricular region of the brain and the distal end is located external of the patient. The wall structure generally includes a biocompatible elastomer material, such as silicone, and a source of one or more occlusion resistant materials at one or both of the proximal and distal ends. In addition to or alternatively, the distal end may have different material properties than the proximal end in order to optimize the resistance to both occlusion and/or infection.

DESCRIPTION

U.S. patent application Ser. No. 11/380,157, Trescony et al, Cerebrospinal Fluid Shunt Having Long Term Anti-Occlusion Agent Delivery, filed Apr. 25, 2006, is incorporated herein by reference in its entirety.

A shunt in accordance with the invention can be used in any medical application where it is necessary to move fluid from one part of the body to another. Examples of types of shunts where the invention can be utilized include, but are not limited to, cardiac shunts, cerebral shunts, glaucoma shunts, urinary catheters, and drainage catheters for trauma or post-surgical applications.

Shunts for treatment of hydrocephalus are well known and have evolved over many decades. Typically, a hydrocephalic shunt includes tubing with a proximal end located in the brain tissue and a distal end located either within the patient at another location external to the brain or external of the patient altogether. Such shunts also typically include a valve structure designed to accommodate and/or control flow based on the intracranial pressure and the position of the patient or other factors. One example includes a valve that is configured for proper flow regulation when the patient is laying down versus standing up.

A shunt may be occluded at three different locations. First, at an entry point such as the proximal location in the brain, second, at or near the valve system, commonly referred to as a "valve obstruction", and third, at the distal end, referred to as a distal catheter occlusion. Shunts, in accordance with one embodiment of this invention, focus on either distal or proximal occlusions rather than valve obstructions, although valve obstructions may be a sequel of occlusions or infection migrating from the distal or proximal ends.

Proximal occlusions are generally more common than distal occlusions, and often result from blood or cellular debris which block the lumen and distal holes on ventricular catheters. This growth may depend on artificial properties (chemistry and geometry) as well as the distance between catheter and tissues in the ventricular (catheter positioning and slit ventricles syndrome). Some ventricular catheter tip designs have been proposed for maintaining the holes of the ventricular catheter away from the walls of the ventricles and the choroids plexus in order to resolve this problem. However, such devices are likely unable to fully prevent proximal occlusion from occurring or may present further problems. Moreover, those known as flanged catheters actually promote firm attachment of the catheter tubing to the choroids plexus. Although distal obstructions are not as frequent as that at the proximal end, shunt-type catheters can be obstructed in the peritoneal cavity by ingrowth of mesothelial cells and fibroblasts.

Shunts of the invention provide long term delivery of one or more occlusion resistant agents. The long term delivery of the one or more occlusion resistant agents is provided through a long term source of the one or more occlusion resistant agents. As used herein, the phrase long term source means that the shunt can deliver at least one occlusion resistant agent for at least 1 year. In another embodiment, the phrase long term source means that the shunt can deliver at least one occlusion resistant agent for at least 5 years. In yet another embodiment, the phrase long term source means that the shunt can deliver at least one occlusion resistant agent for at least 10 years. In a further embodiment, the term long term source means that the shunt can deliver at least one occlusion resistant agent for the entire period in which the shunt is implanted in the patient, or the lifetime of the patient. The long term source of the occlusion resistant agent can be provided by having a refilling port in the shunt, or can be provided from within the shunt itself.

The at least one occlusion resistant agent can be delivered at a level, rate, or concentration that is effective to decrease, diminish, or prevent occlusion. The particular concentration that the occlusion resistant agent is effective at will depend at least in part on the identity of the occlusion resistant agent. Many occlusion resistant agents are effective at a concentration between about 1 nanomolar (nM) and about 1 millimolar (mM). In one embodiment, where the at least one occlusion resistant agent is rapamycin, the concentration where rapamycin is effective is at a concentration of about 1 nM or higher.

Figure 1A:
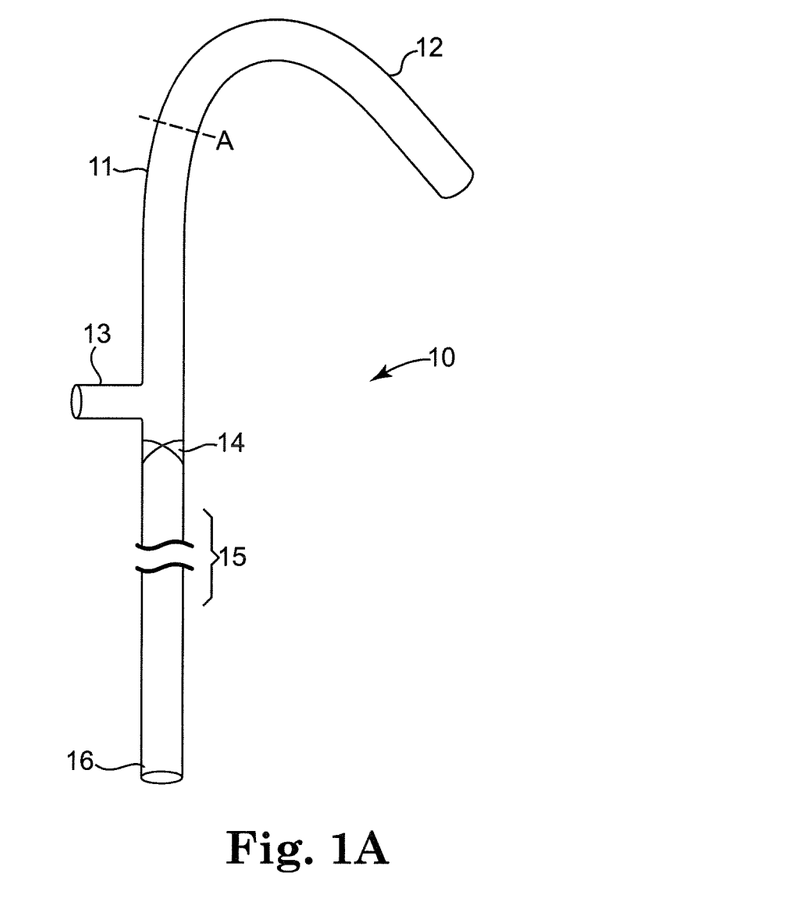
FIG. 1A is a schematic view of one example of a shunt catheter in accordance with the invention.

FIG. 1 shows one embodiment of the hydrocephalic or CSF shunt 10 of the present invention, wherein the shunt 10 includes an elongated conduit 11 having a proximal portion 12, one or more ports 13, one or more valves 14, a central portion 15, and a distal portion 16. The elongated conduit 11 may be of any shape or size, but generally will be in the form of a tube made of an elastomeric material. As noted above, proximal portion 12 is placed in the patient's head at the region of the ventricles while the central portion 15 is routed subcutaneously along the patient's neck and torso. The distal portion 16 may be placed for drainage of the cerebral spinal fluid into the peritoneal cavity where the fluid is then reabsorbed by the normal bodily processes or may extend out of the patients body for external drainage. In yet another embodiment, the distal portion 16 of a shunt 20 in accordance with the invention is connected to a distal catheter that drains cerebral spinal fluid (for example) into another portion of the body.

The elongated conduit 11 can be fabricated from a number of materials, as is known to one of skill in the art having read this specification. Examples of such materials include, but are not limited to poly(L-lactic acid), poly(lactide-co-glycolide), poly(hydroxybutyrate-co-valerate), silicones, polyurethanes, polyesters, vinyl homopolymers and copolymers, acrylate homopolymers and copolymers, polyethers, polyethylene, polypropylene, polycarbonate, polysulfone, cellulosics, polydimethylsiloxanes, methylhydrosiloxane-dimethylsiloxane copolymers, polymethylhydrosiloxanes, polyethylhydrosiloxanes, hydride terminated polyphenyl (dimethylhydrosiloxy)siloxanes, methylhydrosiloxane-phenylmethylsiloxane copolymers, N,-vinylpyrrolidone/methylmethacrylate copolymers, 2-hydroxyethylacrylate (e.g. polymacon), various copolymers of 2-hydroxyethylmethacrylate (e.g, hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.), polyamides, polyimides, fluoropolymers, polytetrafluoroethylenes, natural rubber and polyisoprene.

In the embodiment depicted in FIG. 1A, the port 13 can provide long term delivery of one or more occlusion resistant agents or materials to resist occlusion of the lumenal passage of the shunt. The at least one port 13 can be constructed as would be known to those of skill in the art having read this specification, In one embodiment, the port 13 can include a conventional percutaneous fill port that includes a membrane that can be penetrated by a hypodermic needle and is self-sealing after the needle is removed. In one embodiment, the fluid that is injected from the needle goes through a structure that functions as a funnel to a reservoir The fluid, which generally comprises one or more occlusion resistant agents, flows from the reservoir to the one or more portions of the shunt where occlusion is to be minimized. In one embodiment, a percutaneous fill port also includes a valve to control the rate at which the fluid travels from the reservoir to the one or more portions of the shunt where occlusion is to be minimized. An example of a percutaneous fill port that could function as port 13 can be found in U.S. Pat. No. 5,697,951, the disclosure of which is incorporated by reference herein. Other examples of types of structure that could be utilized as a port 13 include, but are not limited to the center reservoir fill ports of the MEDTRONIC SYNCHROMED® Infusion System and the MEDTRONIC ISOMED® Constant-Flow Infusion System.

The valve 14 can be, but need not be, part of the shunt 20 of the invention. In one embodiment, the valve 14 is a separate component that is configured to be connected to and work with a shunt 20 of the invention. One of skill in the art, having read this specification, will understand the particular types of valves that may be utilized. In embodiments of the invention that are to be used for drainage of cerebral spinal fluid from the brain to another portion of the body, commercially available valves, including, but not limited to, PS Medical Strata® valve, and PS Medical Delta® valve can be utilized.

Figure 1B:
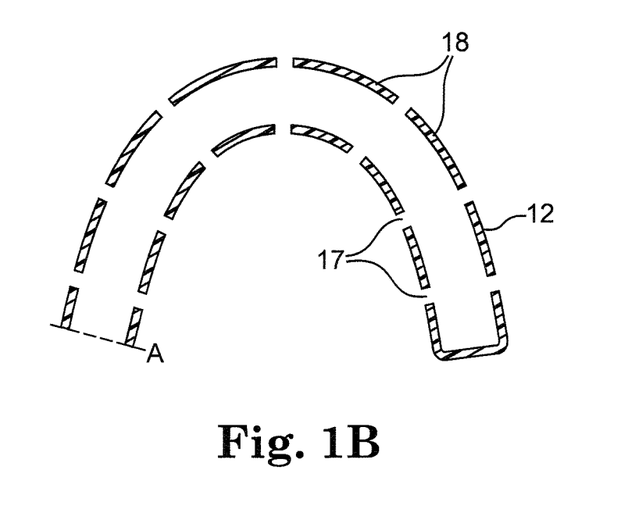
FIG. 1B is a planar cross section of the portion of the shunt depicted in FIG. 1A that is distal of the A axis.
Figure 1C:
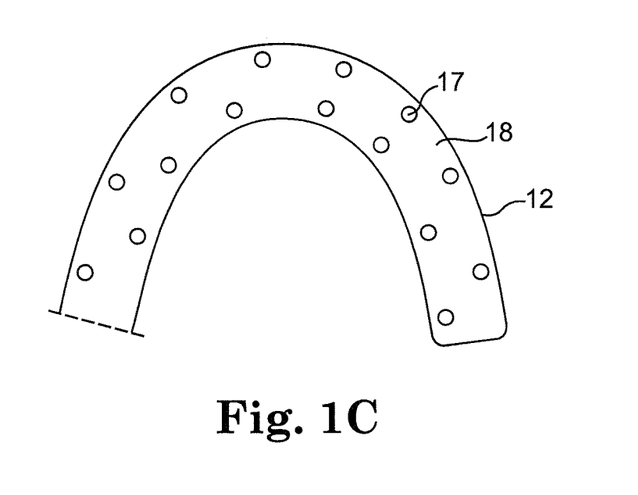
FIG. 1C is a schematic view of the portion of the shunt depicted in FIG. 1A that is distal of the A axis.

In one embodiment, depicted in FIGS. 1B and 1C, the proximal end 12 is at least one of the areas where occlusion is to be minimized. One embodiment of a shunt 10 includes apertures 17 that allow the receipt of bodily fluids, such as CSF into the shunt 10. The wall 18 is generally made of an absorptive material. As used herein, the term "absorptive material" refers to a material that can absorb some amount of at least one occlusion resistant agent. The wall 18 can be constructed of one type of absorptive material, more than one type of absorptive material, or one or more types of absorptive material and one or more other materials. For example, at least the proximal portion 12 can be constructed of one type of absorptive material and can have apertures 17 formed therein. In another embodiment, at least the proximal portion 12 can be constructed of materials that are commonly known to those of skill in the art for shunt construction, and the absorptive material can be added to the proximal portion. In such an embodiment, the absorptive material could be attached to the commonly used shunt materials. Examples of methods of attachment include, but are not limited to, solvent boding, thermal bonding, adhesives, and other methods known to those of skill in the art having read this specification.

In one embodiment, absorptive materials can include any material that can absorb at least some of at least one occlusion resistant agent. In one embodiment, an absorptive material can include a material that has an affinity for the occlusion resistant agent due at least in part by the fact that it is delivered in solution. In another embodiment, absorptive materials can have a selective affinity for at least one occlusion resistant agent. Selective affinities can include gross chemical properties, such as hydrophobic attraction, hydrophilic attraction, or ionic attraction; or more specific affinities such as immuno-based affinity, and molecular imprinting based affinity. Other embodiments can include absorptive materials that have affinities based on gross chemical properties, specific affinities, or any combination thereof. Examples of types of absorptive materials include, but are not limited to, alumina, silica, activated charcoal, cross-linked polystyrene beads, high molecular weight gels such as polyethylene glycol (PEG), silicone polyurethanes, and open-celled foams. One particular example of an open-celled foam that may be useful in embodiments of the invention is a hydrophilic medical grade foam available from Avitar Technologies (Canton, Mass.). These exemplary materials or materials like them could then be modified to provide one or more selective affinities as discussed above. One of skill in the art, having read this specification, would understand and be able to modify such materials in order to alter the affinities thereof in a fashion to make them more or less selective for one or more occlusion resistant agents.

Figure 2A:
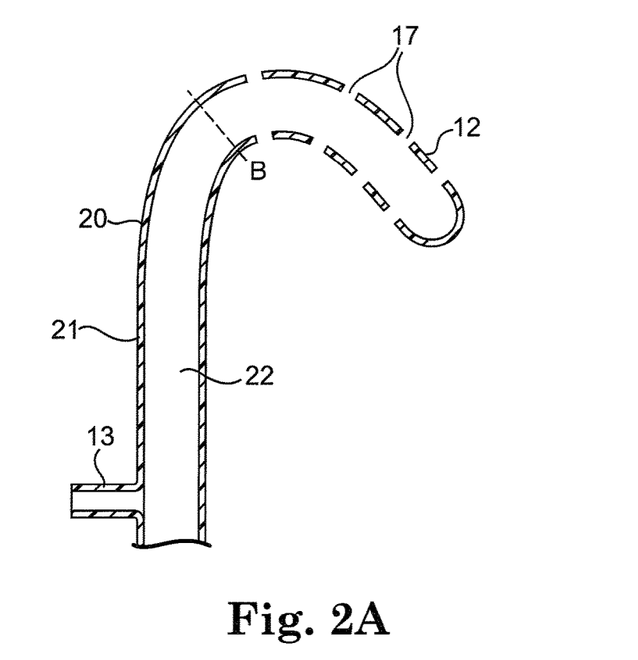
FIG. 2A is a planar cross section of another example of a shunt catheter in accordance with the invention.

A cross section of another embodiment of the invention that can provide long term delivery of one or more occlusion resistant agents is depicted in FIG. 2A. In this embodiment, the elongated conduit 11 of the shunt 20 includes at least two lumens, the fluid conduit 21 and the drainage conduit 22. The drainage conduit 22 is also referred to herein as the CSF drainage conduit 22, because in some embodiments it serves as the conduit for the CSF from the apertures 17 of the proximal portion 12 through the central portion 15 (not shown) to the distal portion (also not shown) where it drains either into another body space of the patient or external to the patient. The fluid conduit 21 is in fluid communication with the port 13. The fluid that is injected into the port 13 can travel from the port 13 into the fluid conduit 21. The fluid, containing the occlusion resistant agent can then permeate through the surface of the fluid conduit 21 so that the occlusion resistant agent is delivered to the space around the shunt 20 in the ventricular space, the volumes within the apertures 17, and the volume within the CSF conduit 22 in at least the proximal portion 12 of the CSF shunt 20.

Although not necessarily depicted in FIG. 2A, the fluid conduit 21 can be used to communicate between the port 13 and the proximal portion 12 of the shunt 20. The fluid conduit 21 can therefore allow for fluid communication throughout the length of the shunt 20.

In such an embodiment therefore, the material that forms the fluid conduit 21 is at least somewhat permeable the one or more occlusion resistant agent. Examples of material that can be used to construct the fluid conduit 21 include, but are not limited to silicone rubber, and polyurethane. In one embodiment, the fluid conduit 21 is made of silicone rubber.

The fluid conduit 21 can have variable properties across its length. For example, it may be advantageous to have thicker walls at some points along the fluid conduit 21 in order to provide structural integrity to particular portions of the proximal portion 12 of the shunt 12 or to slow the passage of the occlusion resistant agent across some portions of the fluid conduit 21. It may also be advantageous to have thinner walls at some points along the fluid conduit 21 in order to increase the rate and/or the amount of occlusion resistant agent that is delivered to the space around some portions of shunt 20. Therefore, in one embodiment of the invention, the thickness of the wall of the fluid conduit 21 can vary over its length. The particular thicknesses, and locations of different thicknesses can be chosen based on a number of factors, including but not limited to, the structural integrity of the shunt 20, a desire to slow passage or decrease the amount of the one or more occlusion resistant agent to some portions of the area around or within the shunt 20, a desire to speed passage or increase the amount of the one or more occlusion resistant agent to some portions of the area around or within the shunt 20, or some combination thereof.

One exemplary embodiment of the invention includes a shunt 20 with a variable wall thickness fluid conduit 21. One example includes a fluid conduit 21 that has a wall that is thinner on the outer surface of the shunt 20 than it is on the inner surface (the surface facing the CSF conduit 22) of the shunt 20. It should also be noted that other properties of the material making up the fluid conduit 21 wall could be modified in order to change the rate and/or amount of occlusion resistant agent that permeates the fluid conduit 21.

Figure 2B:
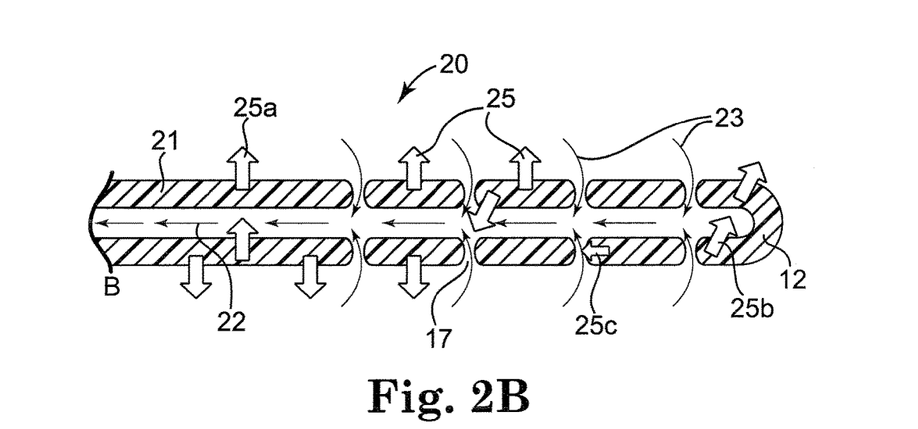
FIG. 2B is a cross section of the portion of the shunt depicted in FIG. 2A that is distal of the B axis.

FIG. 2B illustrates how a shunt in accordance with this embodiment of the invention could function to both drain CSF from the ventricles and release occlusion resistant agent. In this depiction, the CSF flow is represented by the thin arrows, of which some are designated 23. The CSF flows from the space around the shunt 20 through the apertures 17 and into the CSF conduit 22. The flow of the occlusion resistant agent is represented by the thick arrows, of which some are designated 25. The occlusion resistant agent permeates the walls of the fluid conduit 21 and flows into the space around the shunt 20 (exemplified by arrow 25a), the space within the CSF conduit 22 (exemplified by arrow 25b), and into the volume within the apertures 17 (exemplified by arrow 25c). It should be noted that any one or more of the directions of flow of the occlusion resistant agent could be controlled or modified at least in part by changing the thickness of the wall through which that particular flow occurs. For example, to configure a shunt that preferentially flows occlusion resistant agent to the space around the shunt 20 as opposed to flowing occlusion resistant agent to the area within the CSF conduit 22, the outside walls of the fluid conduit 21 could be made thinner than the inside walls (those facing the CSF conduit 22). Such an embodiment may function to minimize the flow depicted by arrow 25b. Other results could also be obtained by varying the wall thicknesses of different areas of the fluid conduit 21.

Another possible embodiment that is similar to that depicted in FIG. 2B is to have a spiral configuration to the apertures in the fluid conduit 21. Such a configuration may provide a compromise between total aperture volume and structural integrity that may be advantageous or desirable.

Another embodiment of the invention includes a shunt 20 that includes a CSF conduit 22, a fluid conduit 21, and absorptive material within the fluid conduit 21. In such an embodiment, the absorptive material can be included in the entire fluid conduit 21, or some portion thereof. In one embodiment, the absorptive material is included in a proximal portion of the fluid conduit 21. In such an embodiment, the fluid that is injected into the fluid conduit 21 via the port 13 would reach the absorptive material via the fluid conduit 21 and the occlusion resistant agent could be absorbed at least in part by the absorptive material.

Another embodiment of the invention includes a shunt 20 that includes a CSF conduit 22, a fluid conduit 21, and a saturated solution containing one or more occlusion resistant agents. In one embodiment, the saturated solution includes at least one carrier fluid, and at least one occlusion resistant agent in solid form. In one embodiment, the at least one occlusion resistant agent is at a concentration that is higher than its solubility in the carrier liquid. In one embodiment, the carrier fluid is water, saline, buffered saline. In one embodiment, the at least one occlusion resistant agent is a hydrophobic compound with a relatively low water solubility. In one embodiment the at least one occlusion resistant agent is a hydrophobic compound with a water solubility of less than about 1 milligram/milliliter (mg/mL).

In an embodiment that includes a saturated solution containing one or more occlusion resistant agents with the occlusion resistant agent at a concentration that is higher than its solubility, an equilibrium will be maintained between the occlusion resistant agent in the saturated solution in the fluid conduit 21 and outside wall of the fluid conduit 21. This equilibrium allows the saturated solution itself to act as a long term source of the at least one occlusion resistant agent. The equilibrium of the occlusion resistant agent and diffusion of the occlusion resistant agent through the wall of the fluid conduit 21 will allow the shunt 20 to deliver an almost constant concentration of the occlusion resistant agent into the area around and within the shunt 20.

Because a large quantity of the occlusion resistant agent can be stored in the fluid conduit 21 by using a saturated solution, the saturated solution can be its own long term source for the occlusion resistant agent, and therefore a shunt 20 that utilizes a saturated solution does not necessarily have to include a port 13.

The inclusion of an occlusion resistant agent in a shunt 20 can be utilized in any region of the shunt. One of skill in the art, having read this specification, would understand how to, for example, utilize a fluid conduit portion in a region other than the proximal portion 12 of the shunt 20. Other regions that could be configured to deliver occlusion resistant agents on a long term basis include the proximal portion 12, the distal portion 18, valve portion 14, or any combination thereof. Generally, the occlusion resistant agent is delivered through portions of the shunt where clotting or tissue growth tends to occlude the lumen of the shunt.

Occlusion resistant agents can include a number of different types of agents that can be selected from multiple classes. Such classes include anti-inflammatory drugs, immuno-suppressive drugs, anti-cancer drugs, anti-proliferatives, anti-migratories, anti-angiogenic drugs, radioactive or radiation-emitting material. Such classes may further include anti-neoplastics, anti-coagulents, anti-thrombogenics, anti-oxidants, cyclooxygenase inhibitors, calcium entry blockers, anti-neoplastics, anti-mitotics, anti-microbials, nitric oxide donors, cell cycle inhibitors, anti-arthritis agents, anti-diabetic agents, thrombin inhibitors, thrombolytics, antibiotics, antiviral agents, antiproliferatives, anti-thrombogenics, anti-oxidants, cyclooxygenase inhibitors, calcium entry blockers, anti-mitotics, anti-microbials, nitric oxide donors, cell cycle inhibitors, anti-cancer agents, and gene therapy agents.

The following classes of anti-occlusion agents with examples in each class are exemplary occlusion resistant agents that can be utilized in the invention. For example classes of anti-occlusion agents that may be utilized in embodiments of the invention include immunosuppressives, anti-inflammatories, anti-neoplastics, anti-angiogenics, anti-coagulants, analgesics, antipyretics, anti-proliferatives, anti-thrombogenics, anti-oxidants, cyclooxygenase inhibitors, calcium entry blockers, anti-neoplastics, anti-mitotics, anti-microbials, antifungals, nitric oxide donors, cell cycle inhibitors, anti-cancer agents, anti-arthritis agents, anti-diabetic agents, thrombin inhibitors, thrombolytics, antibiotics, antiviral agents, and gene therapy agents. The following list provides additional examples of occlusion resistant agents that may be utilized in the invention.

Anti-inflammatory agents that may be utilized in the invention include, but are not limited to selective NF-kappaB modulators, NF-kappaB modulators (non-specific), steroids, infallmatory cytokine inhibitors, P38 inhibitors/stress kinase inhibitors, IL-1 specific inhibitors, TNF specific inhibitors, adhesion inhibitors, chemokines and their receptor inhibitors, MMP inhibitors or other protease inhibitors, NO modulators, non-steroidal anti-inflammatory drugs (NSAIDs), and COX inhibitors.

Non-steroidal anti-inflammatory agents including their racemic mixtures or individual enantiomers where applicable—ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, nepafenac, etodolac, rebamipide, and zaltoprofen.

Other types of not previously categorized anti-inflammatory agents may also be utilized in the invention, examples include, but are not limited to tranilast, rituximab, piroxicam, loxoprofen, doxycyclin, drotrecogin alfa, and tretinoin.

Antineoplastic/antiangiogenic-antimetabolite agents, alkylating agents, cytotoxic antibiotics, vinca alkaloids, mitosis inhibitors, platinum compounds, tissue growth factor inhibitors, cisplatin and etoposide may be used.

Immunosuppressant agents may be cyclosporine A, mycophenolic acid, tacrolimus, rapamycin, rapamycin analogues, such as rapamycin ABT-578 analogue produced by Abbott Laboratories, azathioprine, recombinant or monoclonal antibodies to interleukins, T-cells, B-cells and/or their receptors.

Antithrombogenic factors may be anticoagulents, such as heparin and chondroiten sulfate; platelet inhibitors such as ticlopidine; vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; and thrombolytic agents, such as stretokinase, urokinase and tissue plasminogin activators.

Antiproliferative agents may be paclitaxel, actinomycin D, rapamycin, tacrolimus, everolimus, dexamethasone and rapamycin analogue (ABT-578) produced by Abbott Laboratories.

Analgesics and antipyretics may be the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone.

Antimicrobials may be the cephalosporins such as cephalexin, cefoxytin and cephalothin.

Antifungals may be amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaflate, triacetin, zinc, pyrithione and sodium pyrithione.

Antiviral agents may be acyclovir and acyclovir prodrugs, famcyclovir, zidovudine, didanosine, stavudine, lamivudine, zalcitabine, saquinavir, indinavir, ritonavir, n-docosanol, tromantadine and idoxuridine.

Local anaesthetics may be benzocaine, bupivacaine, amethocaine, lignocaine, lidocaine, cocaine, cinchocaine, dibucaine, mepivacaine, prilocalne, etidocaine, veratridine (specific c-fiber blocker) and procaine.

Other miscellaneous antibiotics may be chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoyiperoxide.

Other pharmaceutical agents may be beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin, analogs, homologs, and derivatives of the above group.

Embodiments of the invention can include one or more of the above exemplified occlusion resistant agents. Embodiments of the invention can also utilize any combination of the above occlusion resistant agents. Embodiments of the invention can also include other agents, including but not limited to, stabilizing agents such as anti-oxidants, radiopaque agents, MRI detectable agents, and ultrasound detectable agents.

An example of the use of one of the occlusion resistant agents is illustrated herein. In an embodiment that includes a saturated solution, one example of an occlusion resistant agent that may be utilized includes rapamycin. Rapamycin is an anti-proliferative agent that can be effective at a concentration of about 1 nM.

Generally, the flow rate of CSF in a young patient (mean 28.7 years old) is 26.6±14.4 ml/hr; and in an elderly patient (mean 77.1 years old) is 11.4±4.2 ml/hr. Therefore, the highest likely flow rate would be 26.6+14.4 m/hr or about 41 ml/hr. If one of skill in the art wanted a CSF shunt with a saturated solution to deliver an effective concentration of rapamycin over the period of 10 years (as an example), the amount of rapamycin that would have to be loaded in the CSF shunt would be about 0.033 g.

$$\frac{914 \text{ g}}{1 \text{ mol}} \times \frac{10 \times 10^{-9} \text{ mol}}{1 \text{ L}} \times \frac{0.041 \text{ L}}{1 \text{ hour}} \times \frac{24 \text{ hours}}{1 \text{ day}} \times \frac{365 \text{ days}}{1 \text{ year}} \times 10 \text{ years} =$$

$$32{,}827{,}224 \times 10^{-9} \text{ g} \approx 0.033 \text{ g}$$

Another method of calculating the amount of rapamycin that would be needed for a CSF shunt containing a saturated solution to deliver an effective concentration over the period of 10 years (an exemplary period of time) follows:

If the rate of formation of CSF is about 500 ml/day, then:

$$10 \text{ yrs} \times \frac{365 \text{ days}}{1 \text{ year}} \times \frac{500 \text{ ml}}{\text{day}} \cong 1{,}825{,}000 \text{ ml} \cong$$

$$1{,}825 \text{ liters of } CSF \text{ formed in 10 years}$$

If it is assumed that the minimal rapamycin concentration (e.g. of rapamycin should be about $1 \times 10^{-8}$ M, then:

$$\frac{10 \times 10^{-9} \text{ moles}}{1 \text{ liter}} \times \frac{914 \text{ g}}{1 \text{ mol}} = \frac{9{,}140 \times 10^{-9} \text{ g}}{1 \text{ liter}}$$

Then the amount of rapamycin necessary for 10 years is:

$$1{,}825 \text{ liters } CSF \times \frac{9{,}140 \times 10^{-9} \text{ g}}{1 \text{ liter}} =$$

$$0.01668 \text{ grams rapamycin} \cong 0.017 \text{ grams rapamycin}$$

If the saturated solution contained 50% solid rapamycin; 10% anti-oxidant stabilizers; 20% radiopacity agents; and 20% fluid (saline, water, etc.), then the volume of saturated solution that would be necessary would be about 0.066 ml (assuming the density of the saturated solution was about 1.0 g/mL). One of skill in the art, having read this specification, will be able to adjust the concentration of the components to achieve iso-osmotic strength relative to CSF fluid to minimize swelling or shrinkage due to osmotic driven transport of water across the device wall.

The invention also includes a system having at least one shunt of the invention. In one embodiment, a system includes a shunt in accordance with the invention, having a valve, and a distal catheter. The invention also includes kits that include at least one shunt of the invention. In one embodiment, a kit includes a shunt in accordance with the invention, a valve, and a distal catheter.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A shunt for at least partial implantation into a patient having a brain with a ventricular region and having an abdomen, comprising:
wherein said at least one occlusion resistant agent permeates through said permeable portion of said fluid conduit into said drainage conduit further comprising a plurality of apertures extending between the proximal end of the drainage conduit and an exterior of the shunt, the plurality of apertures configured to enable passage of the bodily fluids into the drainage conduit without flowing into the fluid conduit.

2. The shunt according to claim 1, wherein said at least one absorptive agent is alumina, silica, activated charcoal, cross-linked polystyrene beads, high molecular weight gels, silicone polyurethanes, open-celled foams or some combination thereof.

3. The shunt according to claim 1, wherein said at least one occlusion resistant agent has a solubility of less than 1 mg/mL in water.

4. The shunt according to claim 1, wherein said at least one occlusion resistant agent is rapamycin.

5. The shunt according to claim 1, wherein said long term source of at least one occlusion resistant agent is a saturated solution that includes said at least one occlusion resistant agent.

6. The shunt according to claim 1, wherein said permeable portion of said fluid conduit has a first location and a second location, and wherein said occlusion-resistant agent permeates at a first rate at said first location and a second rate different from said first rate at said second location.

7. The shunt according to claim 1, further comprising at least one valve.

8. The shunt according to claim 1, further comprising a port in fluid communication with the fluid conduit, wherein the port is configured to receive the occlusion resistant agent and enable the occlusion resistant agent to travel from the port to the permeable portion of the fluid conduit.

9. The shunt according to claim 8, wherein the port comprises a percutaneous access port.

10. The shunt according to claim 8, wherein the port includes a self-sealing membrane configured to receive a needle for injection of the occlusion resistant agent.

11. The shunt according to claim 1, wherein the at least one occlusion resistant agent further permeates through the permeable portion of the fluid conduit into the apertures.

12. The shunt according to claim 1, wherein the at least one occlusion resistant agent further permeates outwardly from the permeable portion of the fluid conduit into the ventricular region of the brain.

* * * * *

UNITED STATES PATENT AND TRADEMARK OFFICE
CERTIFICATE OF CORRECTION

PATENT NO. : 9,861,799 B2
APPLICATION NO. : 12/607419
DATED : January 9, 2018
INVENTOR(S) : Trescony et al.

Page 1 of 1

It is certified that error appears in the above-identified patent and that said Letters Patent is hereby corrected as shown below:

In the Claims

Column 11, Lines 10-20, please replace the language of Claim 1 as follows:
1. A shunt for at least partial implantation into a patient having a brain with a ventricular region and having an abdomen, comprising:
> a drainage conduit for drainage of bodily fluids having a proximal end configured for being implanted in said ventricular region of said brain for receipt of said bodily fluids for flow through said shunt and a distal end for discharge of said bodily fluids from said shunt into said abdomen; and
> a fluid conduit concentric about said drainage conduit having a permeable portion extending along at least a portion of said fluid conduit;
> wherein a long term source of at least one occlusion resistant agent comprises at least one absorptive agent and said at least one occlusion resistant agent is contained within said fluid conduit, wherein said at least one occlusion resistant agent permeates through said permeable portion of said fluid conduit into said drainage conduit further comprising a plurality of apertures extending between the proximal end of the drainage conduit and an exterior of the shunt, the plurality of aperatures configured to enable passage of the bodily fluids into the drainage conduit without flowing into the fluid conduit.

Signed and Sealed this
Eighteenth Day of August, 2020

Andrei Iancu
*Director of the United States Patent and Trademark Office*